US010809256B2

United States Patent
Ohara et al.

(10) Patent No.: US 10,809,256 B2
(45) Date of Patent: Oct. 20, 2020

(54) SIMPLE MEASUREMENT TOOL HAVING REACTION REGIONS SEPARATED BY GEL BOUNDARY REGIONS

(71) Applicant: KAZUSA DNA RESEARCH INSTITUTE FOUNDATION, Kisarazu-shi, Chiba (JP)

(72) Inventors: Osamu Ohara, Kisarazu (JP); Ken Nonaka, Kisarazu (JP)

(73) Assignee: KAZUSA DNA RESEARCH INSTITUTE FOUNDATION, Kisarazu-Shi (JP)

( * ) Notice: Subject to any disclaimer, the term of this patent is extended or adjusted under 35 U.S.C. 154(b) by 579 days.

(21) Appl. No.: 14/426,442

(22) PCT Filed: Oct. 7, 2013

(86) PCT No.: PCT/JP2013/077236
§ 371 (c)(1),
(2) Date: Jun. 30, 2015

(87) PCT Pub. No.: WO2014/057907
PCT Pub. Date: Apr. 17, 2014

(65) Prior Publication Data
US 2016/0011187 A1    Jan. 14, 2016

(30) Foreign Application Priority Data

Oct. 10, 2012  (JP) ................................ 2012-225553

(51) Int. Cl.
*G01N 33/553*    (2006.01)
*G01N 33/543*    (2006.01)

(52) U.S. Cl.
CPC .  *G01N 33/54386* (2013.01); *G01N 33/54326* (2013.01); *G01N 2446/00* (2013.01)

(58) Field of Classification Search
CPC ............................................... G01N 33/54326
USPC .......................................................... 436/526
See application file for complete search history.

(56) References Cited

U.S. PATENT DOCUMENTS

| | | | | |
|---|---|---|---|---|
| 5,565,365 | A * | 10/1996 | Glass ............... | G01N 33/54326 210/222 |
| 5,798,215 | A * | 8/1998 | Cathey ................. | B01F 13/0059 422/504 |
| 5,998,224 | A |  12/1999 | Rohr et al. | |
| 6,121,055 | A * | 9/2000 | Hargreaves .............. | B01L 3/502 435/2 |
| 9,841,421 | B2 * | 12/2017 | Dittmer ............ | G01N 33/54373 |
| 9,863,939 | B2 * | 1/2018 | Wang ................ | G01N 33/54326 |
| 2002/0153251 | A1 * | 10/2002 | Sassi ................ | G01N 27/44743 204/455 |
| 2008/0038810 | A1 * | 2/2008 | Pollack ............. | B01L 3/502761 435/283.1 |
| 2008/0160630 | A1 |  7/2008 | Liu et al. | |
| 2008/0160634 | A1 * | 7/2008 | Su ........................ | G01N 27/745 436/501 |
| 2009/0246782 | A1 * | 10/2009 | Kelso ................ | B01L 3/502761 435/6.16 |
| 2009/0269767 | A1 * | 10/2009 | Soderlund ........... | B01L 3/50273 435/6.11 |
| 2012/0178096 | A1 * | 7/2012 | Beebe .............. | G01N 33/54326 435/6.19 |
| 2013/0043150 | A1 |  2/2013 | Ohashi | |

FOREIGN PATENT DOCUMENTS

JP       2011-232260 A      11/2011
WO    WO 2012/086243 A1     6/2012

OTHER PUBLICATIONS

Shikida et al., "Using wettability and interfacial tension to handle droplets of magnetic beads in a micro-chemical-analysis system", Sensors and Actuators B (2006) 113:563-569.*
English translation of International Preliminary Report on Patentability and Written Opinion dated Apr. 23, 2015, in PCT International Application No. PCT/JP2013/077236.
English translation of International Search Report dated Jan. 14, 2014, in PCT International Application No. PCT/JP2013/077236.

* cited by examiner

Primary Examiner — Christopher L Chin
(74) Attorney, Agent, or Firm — Birch, Stewart, Kolasch & Birch, LLP

(57) ABSTRACT

The purpose of the present invention is to provide a simple measurement tool which can rapidly measure various chemical substances contained in environments or from inside a living body by a simple or inexpensive means/method.
The present inventions relate to, for example, a simple measurement tool for test substances comprising:
 at least two reaction regions, each composed of a water-based liquid, the reaction regions being independent of each other;
 boundary region(s) composed of a gel-type substance that is not or hardly soluble in the water-based liquid;
 a container holding the reaction regions and the boundary region(s); and
 magnetic particles carrying a reactive substance immobilized on a surface thereof,
 in which:
 the reaction regions are separated from each other via the boundary region(s); and
 by using external magnetic field-applying means, the magnetic particles can be substantially exclusively transferred from one reaction region to another reaction region through the boundary region separating these reaction regions, while independence of the respective reaction regions and the respective boundary regions and a function of the magnetic particles being maintained.

15 Claims, 4 Drawing Sheets

SIMPLE MEASUREMENT TOOL HAVING REACTION REGIONS SEPARATED BY GEL BOUNDARY REGIONS

TECHNICAL FIELD

The present invention relates to a simple measurement tool and the like which can perform a reaction treatment step in each reaction region in a closed system by transferring magnetic particles from a reaction region to another reaction region through boundary region separating these regions by using an external magnetic field-applying means, while independence of the respective independent reaction regions and the respective independent boundary regions and a function of the magnetic particles being maintained.

BACKGROUND ART

For various purposes including medical treatments, diagnoses and inspections, health promotion, health care and safety measures, environmental preservation and the like, various chemical substances, biological origin substances such as proteins, sugar, glycoprotein, nucleic acids and the like as well as living bodies such as microorganisms, germs, viruses and the like contained in various samples (specimens) separated/obtained from various environments or living organisms need to be quantitatively or qualitatively measured in medical sites or daily lives.

Particularly, in poor environments with insufficient energy supply such as electricity or the like, physical facilities/equipment, manpower, resources or the like, for example, or in an emergency in which occurrence of an infectious disease, bioterrorism or the like is suspected, for example, it is required that the above-described measurement is performed rapidly by means and methods as simple or inexpensive as possible.

On the other hand, Patent Literature 1 discloses an invention relating to an operating method of a droplet operating micro-device and a droplet made of a water-based liquid containing magnetic particles in the device. The literature describes that this operating method conveys the droplet with the magnetic particles and is used for nucleic acid extraction, refining and gene amplification.

CITATION LIST

Patent Literature

Patent Literature 1: Japanese Patent Laid-Open No. 2011-232260

SUMMARY OF INVENTION

Problems to be Solved by the Invention

Therefore, an object of the present invention is to provide a simple measurement tool which can perform the above-described various measurements rapidly by a simple or inexpensive means/method in order to achieve a desired purpose particularly in the poor environment as described above or in the emergency.

Means for Solving the Problem

In order to solve the above-described problems, the inventors have developed a simple measurement tool and the like as illustrated in each of aspects below as the result of keen study and completed the present invention.

More specifically, the present invention provides the following aspects.

[Aspect 1]

A simple measurement tool for test substances comprising: at least two reaction regions, each composed of a water-based liquid, the reaction regions being independent of each other;

boundary region(s) composed of a gel-type substance that is not or hardly soluble in the water-based liquid;

a container holding the reaction regions and the boundary region(s); and magnetic particles carrying a reactive substance immobilized on a surface thereof, in which:

the reaction regions are separated from each other via the boundary region(s); and by using external magnetic field-applying means, the magnetic particles can be substantially exclusively transferred from one reaction region to another reaction region through the boundary region separating these reaction regions, while independence of the respective reaction regions and the respective boundary regions and a function of the magnetic particles being maintained.

[Aspect 2]

The simple measurement tool according to aspect 1, comprising a plurality of the boundary regions each of which is independent.

[Aspect 3]

The simple measurement tool according to aspect 1 or 2, in which a capacity of the reaction region is 10 to 100 µl.

[Aspect 4]

The simple measurement tool according to any one of aspects 1 to 3, in which, in a moving direction of the magnetic particles, a length of the boundary regions is 2 to 20 mm and a length of the reaction regions is 10 to 80 mm.

[Aspect 5]

The simple measurement tool according to any one of aspects 1 to 4, in which the container is a cylindrical capillary having a diameter of 1.5 to 2.4 mm and a length of 75 to 125 mm.

[Aspect 6]

The simple measurement tool according to any one of aspects 1 to 5, in which the at least two reaction regions are composed of the water-based liquids with compositions different from each other.

[Aspect 7]

The simple measurement tool according to any one of aspects 1 to 6, in which the reactive substance immobilized on the magnetic particles is selected from an antibody, a receptor, an antigen or ligand.

[Aspect 8]

The simple measurement tool according to any one of Aspects 1 to 7, in which the magnetic particles are contained at a range of 10 to 200 µg.

[Aspect 9]

A kit for manufacturing a container, magnetic particles carrying a reactive substance immobilized on a surface thereof, a water-based liquid, a material of a gel-type substance, a gelling agent, sealing means, and the simple measurement tool according to any one of aspects 1 to 8.

[Aspect 10]

A method for measuring a test substance using the simple measurement tool according to any one of aspects 1 to 8, comprising:

(a) adding a sample to a reaction region (first reaction region) located on either one of ends of the simple measurement tool and containing magnetic particles carrying a reactive substance immobilized on a surface thereof, and performing an initial (first) reaction treatment step in the reaction region located on the one end;

(b) transferring the magnetic particles by using external magnetic field-applying means to an adjacent (second) reaction region through a boundary region and performing a subsequent (second) reaction treatment step in the adjacent reaction region;

(c) performing the operation of (b) once or more; and (d) after a last reaction treatment step is completed, measuring a result of the reaction treatment step in any one of the reaction regions.

[Aspect 11]

The method according to aspect 10, in which an antigen-antibody reaction is performed in at least one of the reaction regions.

Advantageous Effect of the Invention

The simple measurement tool of the present invention can be operated extremely simply and can perform various measurements rapidly and quantitatively, semi-quantitatively and qualitatively by using an external magnetic field-applying means even under various poor environments. Moreover, when using the simple measurement tool of the present invention in order to measure test substances, all the reaction treatment steps can be performed in a closed system (sealed state) without adding a reagent, a reaction solution or the like from an outside or without discharging, transferring or the like the reaction solution or the like to the outside and thus, measurement of hazardous substances such as bacteria, pathogenic viruses or the like can be performed safely.

Moreover, the simple measurement tool of the present invention can be of small-sized/light-weighted and/or disposable and thus, transportation thereof is easy and furthermore, measurement can be performed without any special measurement device or the like and thus, it can be used safely and easily even in an outdoor site or the like.

DESCRIPTION OF EMBODIMENTS

The present invention relates to a simple measurement tool including: at least two reaction regions, each composed of a water-based liquid, the reaction regions being independent of each other; boundary region(s) composed of a gel-type substance that is not or hardly soluble in the water-based liquid; a container holding these regions; and magnetic particles carrying a reactive substance immobilized on a surface thereof, in which the reaction regions are separated from each other via the boundary region, and by using external magnetic field-applying means, the magnetic particles can be substantially exclusively transferred from one reaction region to another reaction region adjacent thereto via a boundary region through the boundary region, while independence of the respective reaction regions and the respective boundary regions and a function of the magnetic particles being maintained.

Figure 4:
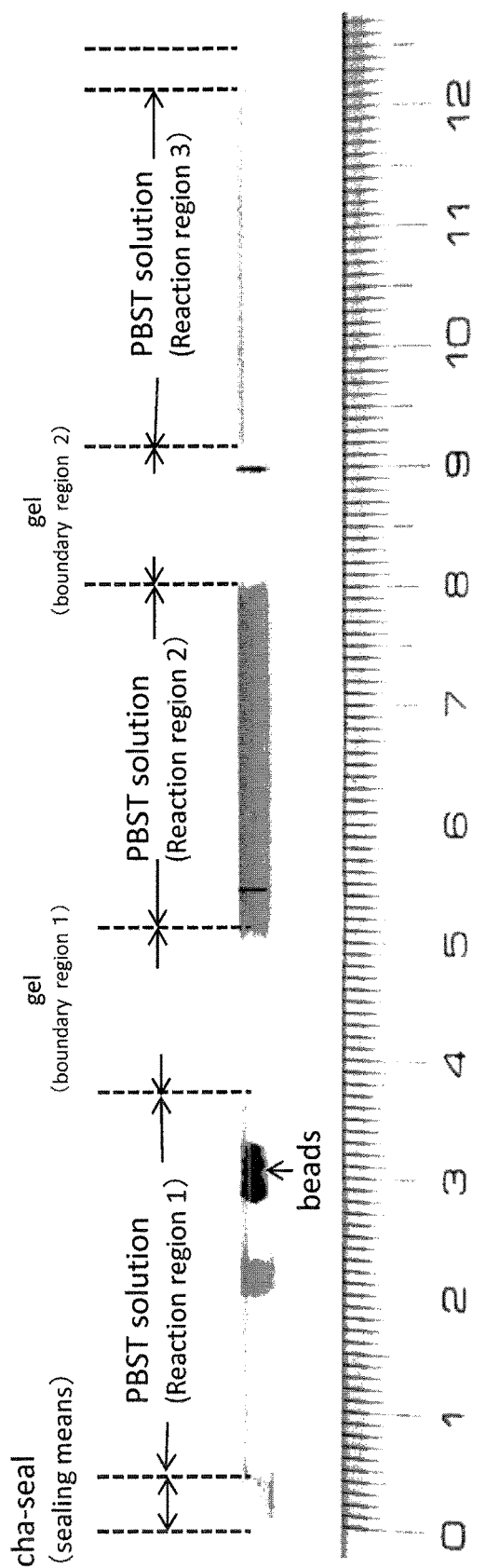
FIG. 4 is a photo of a capillary which is a specific example of the simple measurement tool of the present invention. Its scale (numerals in cm) is indicated on a lower side. It shows cha-seal (Hemato-Seal Tube Sealing compound: white) which is sealing means, a PBST solution (a transparent region marked with a red band in the middle, a black object is beads: reaction region 1), a gel (transparent: boundary region 1), a PNPP (p-Nitrophenyl Phosphate) solution (a region in which yellow color develops after reaction and a black line is marked in the middle: reaction region 2), gel (transparent and marked with a red band in the middle: boundary region 2), and a PBST solution (a transparent region: reaction region 3).

Reaction Region and Boundary Region:

The simple measurement tool of the present invention includes at least two reaction regions composed of a water-based liquid and the boundary region(s) composed of a gel-type substance that is not or hardly soluble in the water-based liquid, and the reaction regions are separated from each other via the boundary region. Therefore, in the case of the simplest measurement tool, each of the regions are included in order of [reaction region 1]-[boundary region 1]-[reaction region 2]. Moreover, if the simple measurement tool includes a plurality of the boundary regions which are independent of each other, it has a configuration such as [reaction region 1]-[boundary region 1]-[reaction region 2]-[boundary region 2]-[reaction region 3], for example. An image of the simple measurement tool of the present invention having such configuration is shown in FIG. 4. As will be described later, at least a part of the water-based liquid constituting the reaction region (first reaction region) located on either one of ends of the container is externally mixed with the sample in advance in measurement and this is added to the first reaction region in some cases and thus, in such a case, the first reaction region of the simple measurement tool of the present invention often includes only a part of the water-based liquid constituting the region.

A capacity of each reaction region can be selected as appropriate by those skilled in the art in accordance with a type of each reaction treatment step or the like performed by using the simple measurement tool of the present invention and it may be different from each other. Considering economy, operability and the like, it can be set within a range of 10 to 100 μl, for example.

Moreover, a thickness of each boundary region (length in a moving direction of magnetic particles) is not particularly limited as long as independence of the boundary region can be maintained (a structure of the boundary region is held) when the magnetic particles are transferred from one of the adjacent reaction regions to the other on an opposite side through the boundary region. Considering types of the water-based liquid and the gel-type substance, operability and the like, the thickness can be set to 2 to 20 mm, for example, and the thicknesses may be different from each other.

Each of the above-described regions is held in an appropriate container and each has independence. As a result, the reaction treatment step in each reaction region of the simple measurement tool of the present invention can be performed in a closed system.

Container

A size, a shape, and a material of the container are not particularly limited as long as the respective reaction regions and the respective boundary regions can be held or divided and moreover, by the external magnetic field-applying means, magnetic particles can be substantially exclusively transferred from one reaction region to another reaction region through the boundary region separating them while the independence of the respective reaction regions and the respective boundary regions and the function of the magnetic particles being maintained.

As a material of such a container, those having light permeability are preferable so that optical detection or the like can be made when measuring absorbance after a desired reaction of the reaction region composed of the water-based liquid, fluorescence, chemoluminescence, bioluminescence, a change of refractive index and the like.

Moreover, in order to transfer only the magnetic particles by the external magnetic field-applying means from one reaction region to another reaction region through the boundary region separating them, an inner surface of the container is preferably a smooth surface, and a surface roughness is preferably Ra=0.1 μm or less, for example.

Considering the above-described conditions, heat resistance, water repellency required in transfer of a droplet, adhesive property, workability, inexpensiveness and the like, a material of the container is preferably glass and resins such as polyethylene, polypropylene, polystyrene, polycarbonate, Teflon (registered trademark) and the like, for example, in view of strength, operability, economy and the like.

Moreover, as a shape of the container, an elongated cylindrical capillary, a flat-plate type chip having a flow passage therein in which each reaction region and each boundary region are formed, or the like is preferable. Such a capillary is assumed to have a diameter of 1.5 to 2.4 mm and a length of 75 to 125 mm, for example, and can be used as a micro-device or a microchip. Moreover, in the case of a capillary made of glass, for example, a thickness of the glass is usually approximately 0.3 to 0.7 mm. Therefore, when using such an elongated cylindrical capillary, a thickness (length in the moving direction of the magnetic particles) of each reaction region composed of a water-based liquid is usually 10 to 80 mm.

At least one of both ends of the container is closed by arbitrary appropriate sealing means known to those skilled in the art. Such sealing means may be such that one end of the container itself is simply closed without using a special material, for example. Moreover, if the first reaction region located on either one of ends of the container, to which region a sample or a water-based liquid containing it is added, is to be also closed by the sealing means, the sealing means used for that needs to be capable of being opened/closed (detachable). As such sealing means, a filler made of an appropriate material (made of a resin, for example), can be used to fill an opening portion and removed as appropriate, for example. An end of the container on a side of the first reaction region to which the sample or the water-based liquid containing it is added does not have to be particularly closed by the sealing means when using the simple measurement tool of the present invention in order to measure a test substance.

Water-Based Liquid:

The water-based liquid is to provide a venue for various reactions in the reaction region and can include various compounds involved in the reaction or a component thereof as a component in addition to its function as a mere medium of the reaction. For example, it can be exemplified as a substance which reacts with a reactive substance immobilized on the magnetic particle surface, a substance which further reacts with a substance bonded to the magnetic particle surface by this reaction, various buffers known to those skilled in the art, surfactants, salts, and other various auxiliary agents, reaction reagents, fluorescence, organic solvents such as alcohol and the like. Moreover, the water-based liquids can be provided in arbitrary forms such as water, aqueous solutions, aqueous suspensions and the like.

Types and compositions (pH, component concentration and the like) of the water-based liquids can be selected as appropriate by those skilled in the art in accordance with environments, purposes and the like for using the simple measurement tool of the present invention as well as a type or the like of each reaction treatment step performed by using the simple measurement tool of the present invention. Moreover, the types and compositions of the water-based liquids constituting each reaction region may be the same or different.

Gel-Type Substance:

In the simple measurement tool of the present invention, the boundary region separating the two reaction regions is composed of a gel-type substance that is not or hardly soluble in the water-based liquid. That is, the gel-type substance means a chemically inactive substance which does not have a chemical influence on the water-based liquid whether it is during execution of the reaction treatment step in the reaction region composed of the water-based liquid or not. The gel-type substance in the present invention is preferably in a sol state before being filled in the container. Usually, after a gelling agent is added to the liquid substance that is not or hardly soluble and the liquid substance is filled in the container, the liquid substance can be easily gelled by lowering a temperature to a gel-sol transition point or less.

The boundary region composed of the gel-type substance prepared as above needs to have a physical characteristic that can substantially exclusively transfer the magnetic particles from one reaction region to another reaction region through the boundary region while independence of the respective reaction regions and the respective boundary regions and the function of the magnetic particles being maintained. For example, storage viscoelastic modulus E' in dynamic viscoelastic modulus is preferably 10 to 100 kPa or more preferably 20 to 50 kPa at a normal temperature (20° C.±15° C.) or less.

Therefore, as the liquid substance that is not or hardly soluble, one type or two types or more selected from a group consisting of oily substances whose solution to water at 25° C. is roughly 100 ppm or less and in a liquid state at the normal temperature (20° C.±15° C.) or various liquid oil, ester oil, hydrocarbon oil, and silicone oil, for example, which are known to those skilled in the art can be used in combination.

For example, various types of plant oil and the like as the liquid oil, mineral oil, liquid paraffin and the like as the hydrocarbon oil, and dimethypolysiloxane, methylphenyl-polysiloxane and other phenyl-group containing silicone oil, methylhydrogenpolysiloxane and the like can be cited as the silicone oil.

As the gelling agent, one type or two types or more of arbitrary oily gelling agents which are known to those skilled in the art and are selected from a group consisting of hydroxyl fatty acid, dextrin-fatty acid ester, glycerin-fatty acid ester and the like can be used in combination.

As the hydroxy fatty acid, hydroxystearic acid (12-hydroxystearic acid by Wako Pure Chemical Industries Co., Ltd.), dihydroxystearic acid, and ricinoleic acid are preferable, for example.

As the dextrin-fatty acid ester, dextrin myristate (product name: "Rheopearl MKL", by Chiba Flour Milling Co., Ltd.), dextrin palmitate (product name: "Rheopearl KL", "Rheopearl TL", both by Chiba Flour Milling Co., Ltd.), (palmitic acid/2-ethylhexanoate) dextrin (product name: "Rheopearl TT", by Chiba Flour Milling Co., Ltd.) and the like can be cited, for example.

Moreover, as the glycerin-fatty acid ester, glyceryl behenate, glyceryl octastearate, glyceryl eicosanoate and the like can be cited, and one type or more of them may be used in combination. Specifically, the product name "TAISET 26" (by Taiyo Kagaku Co., Ltd.) containing 20% glyceryl behenate, 20% glyceryl octastearate and 60% hardened palm oil, the product name "TAISET 50" (by Taiyo Kagaku Co., Ltd.) containing 50% glyceryl behenate and 50% glyceryl octastearate and the like can be cited.

A content of the gelling agent to be added to the liquid substance that is not or hardly soluble can be determined as appropriate by those skilled in the art in accordance with the type or the like, and it can be 0.1 to 0.5 weight %, 0.5 to 2 weight % or 1 to 5 weight % to the total weight of the liquid substance.

Gelling can be performed by an arbitrary method known to those skilled in the art. For example, it can be performed such that the liquid substance that is not or hardly soluble is heated, the gelling agent is added to the heated liquid substance and then, cooled after the gelling agent is fully solved. A heating temperature may be determined as appropriate by considering the physical characteristics of the liquid substance and the gelling agent to be used. It is preferably set to 60 to 80° C., for example, in some cases. Dissolution of the gelling agent is preferably performed by gently being mixed. Cooling is preferably performed slowly. As an aspect to which a preferred aspect of the above-described gelling method is applied, an aspect using the above-described TAISET 26 (by Taiyo Kagaku Co., Ltd.) can be cited, for example.

The sol-gel transition point can vary depending on the conditions such as the type of oil, the type of the gelling agent, an added amount of the gelling agent and the like. Therefore, each of the conditions is selected as appropriate by those skilled in the art so that a desired sol-gel transition point can be achieved. The sol-gel transition point can be set so as to be 40 to 50° C., for example.

Magnetic Particles:

Such magnetic particles are not particularly limited as long as they are particles responding to magnetism, and particles having a magnetic body such as magnetite, γ-iron oxide, manganese zinc ferrite and the like can be cited, for example. A surface of the magnetic particle is preferably coated with a hydrophilic group such as a hydroxyl group, an amino group, a carboxyl group, a phosphate group, a sulfonate group and the like.

With regard to the size of the magnetic particle having a hydrophilic group on the surface, the average particle size can be approximately 0.1 to 500 μm. The small average particle size is not preferable because the magnetic particles tend to be present in a state diffused in the droplet.

In the magnetic particles used in the present invention, a reactive substance is immobilized on the surface thereof, and magnetic particles are substantially exclusively transferred by the external magnetic field-applying means to each reaction region, where they are subjected to various reaction treatment steps. An amount of the magnetic particles used in the present invention is preferably within a range of 10 to 200 μg in usual if a measurement tool is an elongated cylindrical capillary having a capacity of each reaction region as described above, for example, though it depends on various conditions such as the types of the test substances as a measurement target and of the reaction treatment step in each reaction region, a capacity of each reaction region and the like.

That is, on the surface of the magnetic particles, the reactive substance having an appropriate chemical structure known to those skilled in the art, such as an antibody (labelled antibody, for example), a receptor, an antigen, a ligand and the like is immobilized through arbitrary bonding means known to those skilled in the art, such as an amino group, a carboxyl group, an epoxy group, avidin, biotin, digoxigenin, protein A, protein G and the like or directly through covalent bonding, electrostatic force, Van der Waals force and the like, for example. The test substance as the measurement target is directly or indirectly bonded to the reactive substance by the reaction treatment step and the like and can be selectively adsorbed by or immobilized on the surface of the magnetic particles in the end.

The magnetic particles may be contained in advance in the reaction region located on either one of the ends of the simple measurement tool of the present invention or may be independent of the simple measurement tool as it is or in a form contained in the water-based liquid added to the reaction region. If they are provided as a kit for fabricating the simple measurement tool of the present invention, they can be included in the kit together with the container and other materials.

Reaction Treatment Step

The measurement method of the present invention includes:

(a) adding a sample to a reaction region (first reaction region) located on either one of ends of the simple measurement tool and containing magnetic particles composed of a reactive substance immobilized on a surface thereof, and performing an initial (first) reaction treatment step in the reaction region located on the one end;

(b) transferring the magnetic particles to an adjacent (second) reaction region through a boundary region by using an external magnetic field-applying means and performing a subsequent (second) reaction treatment step in the adjacent reaction region;

(c) performing an operation of (b) once or more (the operation of (b) is repeated as necessary); and (d) after the last reaction treatment step is finished, measuring a result of the reaction treatment step in any one of the reaction regions. That is, if the simple measurement tool of the present invention having a configuration of [reaction region 1]-[boundary region 1]-[reaction region 2]-[boundary region 2]-[reaction region 3] is used, after the operation of (b) is performed twice and the last reaction treatment step in the [reaction region 1] or the [reaction region 3] is finished, the result of the reaction treatment step in either one of the reaction regions is measured in accordance with a reaction form, type and the like.

The sample can be added to a first reaction region after external pre-treatment with at least a part (it does not have to include the magnetic particles carrying the reactive substance immobilized on the surface thereof) of the water-based liquid constituting the first reaction region or can be directly added to the first reaction region containing the magnetic particles. Moreover, reaction time in each reaction region, holding time and moving speed of the magnetic particles and the like can be set as appropriate by those skilled in the art in accordance with the type of each reaction, an environment (temperature, humidity and the like) in which the simple measurement tool is used and the like. Moreover, the reaction treatment step can be also performed by attaching the simple measurement tool of the present invention to an appropriate device such as a rotator or the like and by diffusing the magnetic particles in each reaction region in the water-based liquid for appropriate time, for example.

As reactions performed in each reaction region, various arbitrary reactions known to those skilled in the art or chemical reactions such as binding reaction, decomposition reaction, chromogenic reaction, color reaction, oxidizing/reduction reaction and the like as well as immunity system biochemical reaction such as synthetic system, catalytic system, metabolic system, and antigen/antibody reaction of living substances such as nucleic acid, protein, fat, sugar and the like can be cited. Moreover, as a treatment step not accompanied by chemical changes of compounds, various treatments such as the pre-treatment performed prior to the reaction, sorting (separating) treatment, dissolution treatment, mixing treatment, dilution treatment, stirring treatment, washing treatment, temperature adjustment (heating and cooling) treatment and the like can be cited, for example. The reaction treatment step performed in at least the two reaction regions may be the same type or may be different from each other.

Therefore, by using the simple measurement tool of the present invention, all the prior-art known arbitrary measurement methods (assay-based) each consisting of a series of steps can be continuously performed in a closed system. For example, in the case of performing the ELISA method, magnetic particles are substantially exclusively transferred sequentially to the respective reaction regions through the boundary region separating the respective reaction regions by the external magnetic field-applying means so that an antigen reaction between a first antibody immobilized on the magnetic particle surface and an antigen to be tested (test substance) in the sample is performed in a first reaction region, the washing treatment is performed in a second reaction region, the antigen reaction is performed between an enzyme-labelled secondary antibody and the antigen to be tested in a third reaction region, the washing treatment is performed again in a fourth reaction region, a chromogenic reaction is performed for a certain time between the enzyme bonded to the secondary antibody immobilized on the magnetic particle surface and a chromogenic substance contained in the water-based liquid in the reaction region lastly in a fifth reaction region and moreover, after the magnetic particles are transferred to a sixth reaction region and the last reaction treatment step (mixing, for example) is performed as necessary and then, a reaction result in the fifth reaction region can be quantitatively measured. As a result, though a reaction stopping reagent such as sodium hydroxide or the like needs to be newly added in the prior-art method in order to stop coloring by the coloring reagent in certain time, in the reaction system using the simple measurement tool of the present invention, transfer of the magnetic particles stops the reaction and thus, the reaction result can be obtained easily in the closed system.

As the external magnetic field-applying means, arbitrary means known to those skilled in the art can be used. For example, a so-called portable magnet or an appropriate magnetic-field generating device or the like can be cited. In order to transfer the magnetic particles by the magnetic field-applying means in the simple measurement tool of the present invention, an appropriate method such as moving of a portable magnet manually or the like or moving of the simple measurement tool of the present invention in the above-described magnetic field generating device or the like can be performed. However, as already described above, when the magnetic particles are transfer by the external magnetic field-applying means from one of adjacent reaction regions to another adjacent reaction region on the opposite side through the boundary region, independence of the boundary region needs to be maintained (the structure of the boundary region needs to be held).

The sample is an arbitrary substance (composition) which has a possibility of containing a test substance separated/obtained in various environments or from inside a living body by an appropriate method or derived from the living body and treated or processed as appropriate in accordance with a purpose.

After the last reaction treatment step of the measurement method using the simple measurement tool of the present invention is finished, the result of the reaction treatment step in any one of the reaction regions is measured by an arbitrary appropriate external measurement device or means known to those skilled in the art such as a spectrophotometer, for example, by which the test substance contained in the sample can be measured qualitatively, semi-quantitatively or quantitatively. In the case of a qualitative reaction, visual measurement can be also made.

The present invention also relates to a kit for fabricating the above-described simple measurement tool. The kit includes the container, the magnetic particles with a reactive substance immobilized on the surface thereof, the container and water-based liquid included in the kit, the material of the gel-type substance, the gelling agent, sealing means, the magnetic field-applying means, tools for pre-treatment (mixing, for example) for the sample and water-based liquid and the like as necessary. Moreover, in the kit of the present invention, the liquid substance and the gelling agent may be provided in the already mixed or gelled state or the liquid substance before gelling and the gelling agent may be provided as separate elements.

EXAMPLE

The present invention will be described below by referring to examples, but these examples exemplify specific aspects of the present invention and the technical scope of the present invention is not limited by them. Abbreviations used in this Description are as follows:
BSA: bovine serum albumin;
PBS: phosphate buffered saline:
PBST solution: 0.02% Tween 20 containing phosphate buffered saline; and
AP conjugate Goat anti-mouse IgG: alkaline phosphatase bonding goat origin anti-mouse IgG antibody Reference Example 1

Fabrication of 12-HSA Gel-Filled Capillary

A 12-HSA gel solution was made by adding 0.005 g of 12-hydroxystearic acid (by Wako Pure Chemical Industries Co., Ltd.) and incubating it at 80° C. (the gel was prepared beforehand and continuously incubated at 80° C. until it is filled). A 5% BSA/PBS (5% bovine serum albumin containing phosphate buffered saline) solution was filled in a ring cap tube (200 µL) and immersed for an hour and then, the solution was drawn out and the tube was washed with distilled water and then, an inside of the ring cap tube was dried by nitrogen. An opening on one of ends of the ring cap was closed by cha-seal (Hemato-Seal Tube Sealing compound), while the reagent was filled from the other end.

Figure 1:
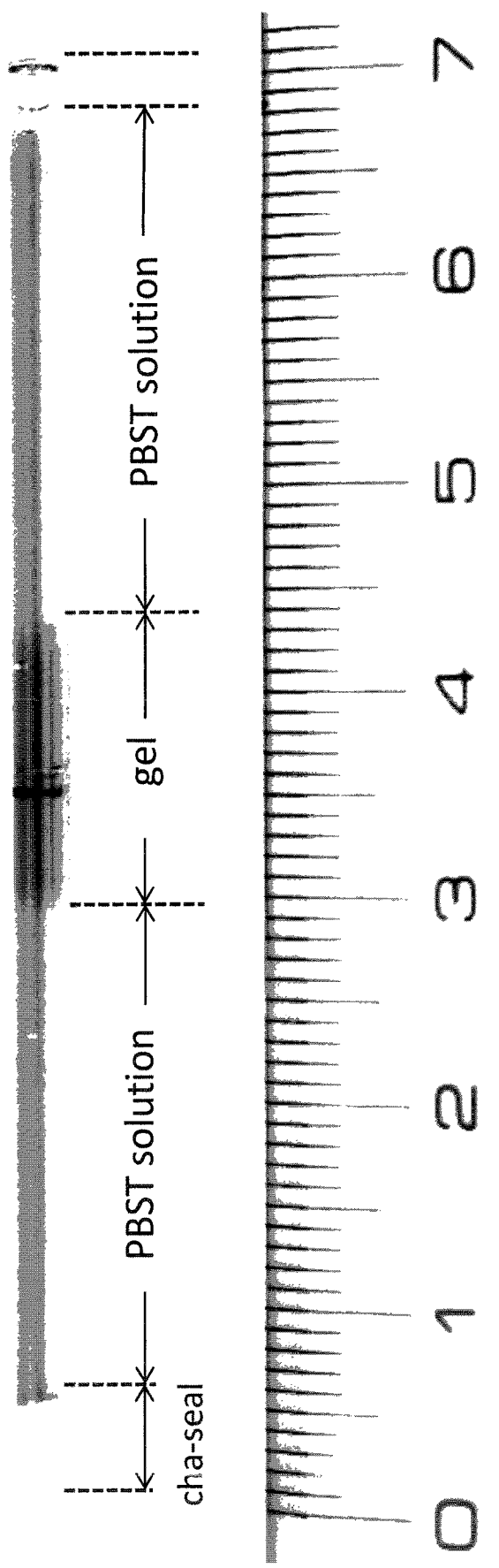
FIG. 1 is a photo of a capillary simulating a simple measurement tool of the present invention. Its scale (numerals in cm) is indicated on a lower side. It shows cha-seal (Hemato-Seal Tube Sealing compound: white), a PBST solution (PBST, 0.02%, Tween 20-containing phosphate buffered saline: pale blue), a gel (brown), and a PBST solution (pale blue) in order from left to right. A pigment is added to the solutions and the gel for visualization.

As an order of filling, 80 μl of the PBST solution was filled and then, 20 μl of the 12-HSA (0.5% w/v) solution having been incubated at 80° C. was filled and lastly, 80 μl of the PBST solution was filled. The filling was performed in a perpendicularly standing state, and attention was paid so that air is not caught during filling. After the gel is filled, it was left for 15 minutes and then, the last PBST solution was added. A schematic view of a gel-filled capillary (simple measurement tool of the present invention) prepared as above is shown (FIG. 1). Since solvent and the gel had no color and were hard to see, they were colored (pale blue for the solvent and brown for the gel). The right end is closed by cha-seal, while the left end is left open.

Reference Example 2

Fabrication of TAISET 26 Gel-Filled Capillary

A TAISET 26 gel solution was made by adding 0.012 g of TAISET 26 (by Wako Pure Chemical Industries Co., Ltd.) to 1 ml of silicone oil KF-56 (by Shin-Etsu Chemical Co., Ltd.) and incubating it at 70° C. (the gel was prepared beforehand and continuously incubated at 80° C. until it is filled). A 5% BSA/PBS solution was filled in a ring cap and immersed for an hour and then, the solution was drawn out and the tube was washed with distilled water and then, an inside of the ring cap tube was dried by nitrogen. An opening on one of ends of the ring cap was closed by cha-seal, while the reagent was filled from the other end.

As an order of filling, 80 μl of the PBST solution was filled and then, 20 μl of the TAISET 26 (1.2% w/v) solution having been incubated at 70° C. was filled and lastly, 80 μl of the PBST solution was filled. The filling was performed in a perpendicularly standing state, and attention was paid so that air is not caught during filling. After the gel is filled, it was left for 15 minutes and then, the last PBST solution was added.

Comparative Example 1

Fabrication of PBST Filled Capillary

The 5% BSA/PBS solution was filled in a ring cap and immersed for an hour. Then, the solution was drawn out and the tube was washed with distilled water and then, an inside of the ring cap tube was dried by nitrogen. An opening on one of ends of the ring cap was closed by cha-seal, while 180 μl of the PBST solution was filled from the other end. The filling was performed in a perpendicularly standing state, and attention was paid so that air is not caught during filling.

Reference Example 3

Preparation of AP (Alkaline Phosphatase) Conjugate Goat Anti-Mouse IgG Immobilized on Beads (Magnetic Particles) (for Checking Quantitative Change)

Protein G coating magnetic beads (by DYNAL) was subjected to vortex and suspension and then, dispensed to each tube by 3 μl each, and 100 μl of the PBST solution was added and subjected to vortex and then, it was centrifuged (1000 rpm, 5 seconds), and the tube was stood on a magnetic stand (by Life technologies) and left as it is for 5 minutes and then, the solution was drawn out by paying attention so that the magnetic beads were not sucked in. After this step was repeated twice, 198 μl of the PBST solution was added. Subsequently, 2 μl of the AP (alkaline phosphatase) conjugate Anti-Mouse IgG (by Promega) whose concentration was changed by 10 dilution magnification as follows (a to f) was added to each tube and mixed for 2 seconds and stirred on the rotator at a room temperature for 15 minutes and then, centrifuged (100 rpm, 5 seconds), the tube was stood on the magnetic stand and the magnetic beads were caught (5 minutes) and then, the solution was drawn out so that the magnetic beads were not included. Since this beads washing protocol is common to the following reference examples, hereinafter it is referred to as a magnetic beads washing work.

200 μl of the PBST solution was added, and the magnetic beads washing work was performed again.

AP conjugate Anti-Mouse IgG dilution concentration (IgG final concentration)
a) 1000 ng/μl (final conc. 10000 pg/μl)
b) 100 ng/μl (final conc. 1000 pg/μl)
c) 10 ng/μl (final conc. 100 pg/μl)
d) 1 ng/μl (final conc. 10 pg/μl)
e) 0.1 ng/μl (final conc. 1 pg/μl)
f) 0.01 ng/μl (final conc. 0.1 pg/μl)

Reference Example 4

Check of Quantitative Change of AP Conjugate Goat Anti-Mouse IgG Immobilized on Beads A PNPP coloring reagent (by Thermo) in 100 μl was added to each AP conjugate Goat anti-mouse IgG immobilized on beads prepared in the reference example 3 and subjected to vortex and then, an alkaline phosphatase reaction was performed on a tube mixer (by TOMY) at a room temperature for 15 minutes. Then, 50 μl of a reaction stopping agent (2N sodium hydroxide aqueous solution) was added and well mixed and then, lightly centrifuged (1000 rpm, 5 seconds), the tube was stood on the magnetic stand and left as it is for 5 minutes and then, 50 μl of the reaction solution was drawn out, and absorbance was measured by BioSpec-nano (by Shimadzu Corporation) (wavelength: 405 nm).

Figure 2:
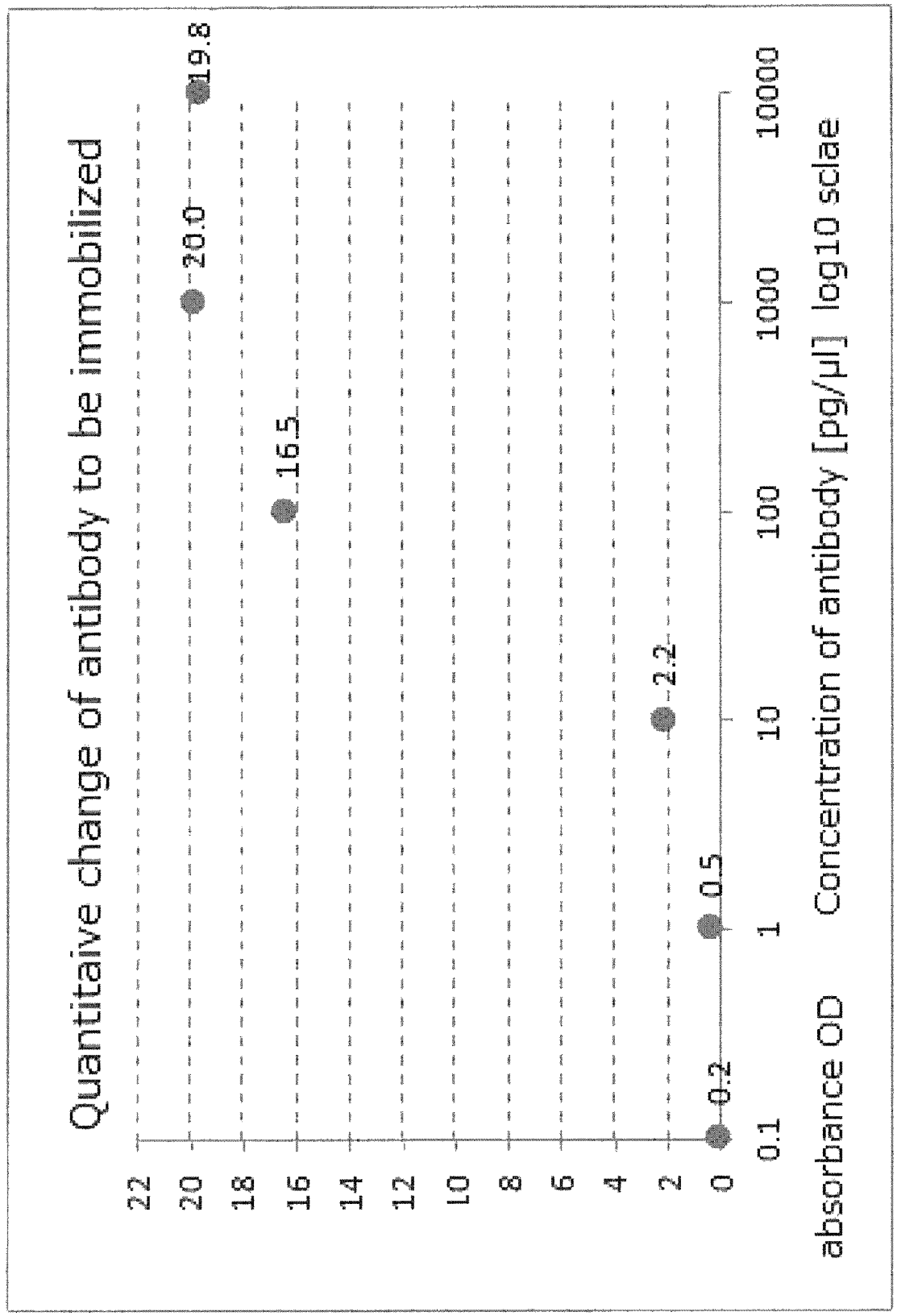
FIG. 2 shows a result of confirmation of quantitative change of AP (alkaline phosphatase) conjugate Goat anti-mouse IgG to be immobilized on beads.

A result of a quantitative analysis of the AP conjugate Goat anti-mouse IgG (FIG. 2) reached an observation upper limit (saturated) value at a and b (reaction system of 1 ng/μl or more) and at an observation lower limit value or less at e and f (reaction system of 1 pg/μl or less) when the PNPP coloring reagent was used. As a result, it was confirmed that a range within which a concentration change can be confirmed is a range from 1 pg/μl to 1 ng/μl. From this result, concentration of the AP conjugate Goat anti-mouse IgG used in an experiment about an influence of gel passage on the antibody immobilized on the beads by was set to concentration (50 pg/μl) at which a concentration change can be quantified.

Reference Example 5

Preparation of AP Conjugate Goat Anti-Mouse IgG Immobilized on Beads (for Examination)

Protein G coating beads (by DYNAL) was subjected to vortex and suspension and then, dispensed to each tube by 3 μl each, and 100 μl of the PBST solution was added and mixed and then, the magnetic beads washing work was performed.

After this washing work was performed twice, 198 μl of the PBST solution (tween20 0.02%) was added, and subsequently, 2 μl of the AP conjugate Anti-Mouse IgG (by Promega) at 0.05 ng/μl was added. Subsequently, it was mixed on the rotator at a room temperature for 15 minutes and then, the magnetic beads washing work was performed. After 200 μl of the PBST solution was added to and mixed with the recovered magnetic beads, the magnetic beads washing work was performed.

After this beads washing work was performed twice, 20 µl of the PBST solution was added. The magnetic beads (by Roche) for gel leading was added in 3 µl to each tube in the second washing and washed together.

Reference Example 6

Check of Influence by Gel Passage of AP Conjugate Goat Anti-Mouse IgG Immobilized on Beads The Goat anti-mouse IgG AP immobilized antibody beads solution prepared in the reference example 5 was added to the reference examples 1 and 2 and the magnetic beads prepared in the comparative example 1 to each capillary in full amounts.

The capillary of the comparative example 1 was used as control. After the beads were added, the beads were reciprocated three times vertically (horizontally) by a magnet through the capillary tube, the tube with 100 µl of the PBST solution therein was arranged at an opening portion, and the beads were discharged therein.

In the case of the 12-HSA gel-filled capillary in the reference example 1, too, after the beads are reciprocated three times (passage through the gel six times) vertically (horizontally) by a magnet through the capillary tube, the tube with 100 µl of the PBST solution therein was arranged at an opening portion, and the beads were discharged therein.

After the beads are reciprocated three times (passage through the gel six times) vertically (horizontally) by a magnet through the capillary tube after beads-apply by using the TAISET 26 gel-filled capillary in the reference example 2, the tube with 100 µl of the PBST solution therein was arranged at an opening portion, and the beads were discharged therein.

After the magnetic beads washing work was performed for the respective discharged beads, 100 µl of the PNPP coloring reagent (by Thermo) was added and subjected to vortex and then, an alkaline phosphatase reaction described in the reference example 4 was performed on the tube mixer at a room temperature for 15 minutes. Then, 50 µl of the reaction stopping agent (2N sodium hydroxide aqueous solution) was added and mixed and then, centrifuged (1000 rpm, 5 seconds), the tube was stood on the magnetic stand and left as it is for 5 minutes, and 50 µl of the reaction solution was drawn out, and absorbance was measured by BioSpec-nano (by Shimadzu Corporation) (wavelength: 405 nm).

Figure 3:
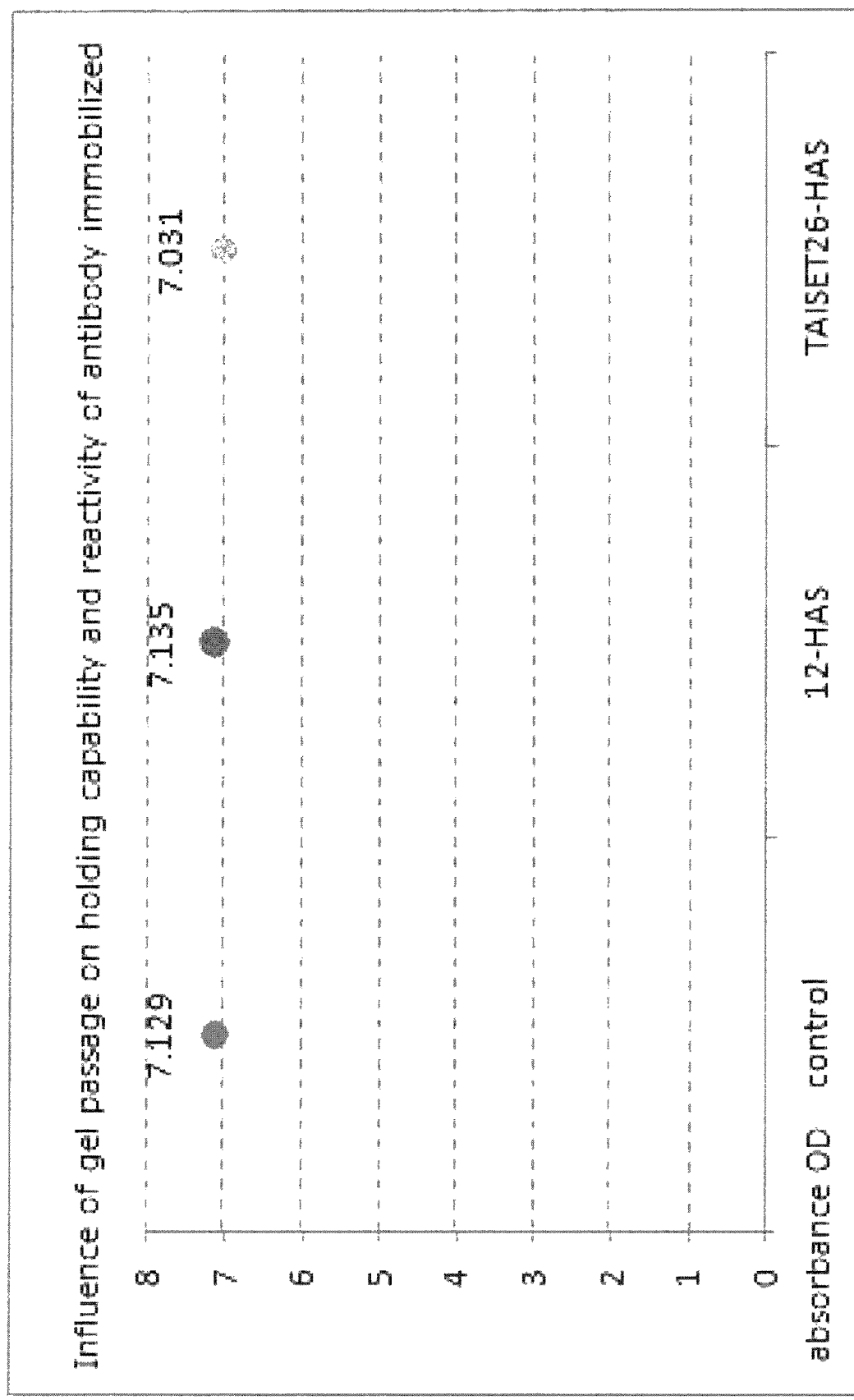
FIG. 3 shows a result of confirmation of an influence by gel passage of the AP (alkaline phosphatase) conjugate Goat anti-mouse IgG immobilized on beads.

As the result of measurement of the above-described three samples, it was confirmed that absorbance measured values of the beads having been passed through the capillary as control and those of the beads measured through the gel indicated substantially equal numerical values (reference example 1: 7.135, reference example 2: 7.031, comparative example 1: 7.129) (FIG. 3). That is, it was confirmed that holding capability of AP conjugate Goat anti-mouse IgG by Protein G is not influenced by passage through the gel, and measurement is not influenced, either, by passage through the gel.

Example 1

Construction of System in which Reaction is Completed in Capillary

On the basis of the above-described results, an example of the simple measurement tool of the present invention was fabricated as follows. That is, an opening on one of ends of the ring cap (200 µl) subjected to BSA blocking similarly to the reference example 2 was closed by cha-seal, while the reagent was filled from the other.

As an order of filling, 80 µl of the PBST solution [reaction region 1] and then, 15 µl of the TAISET26 (1.2% w/v) solution having been incubated at 70° C. was filled [boundary region 1], 40 µl of the PNPP coloring reagent was filled [reaction region 2], 15 µl of the TAISET26 (1.2% w/v) solution having been incubated at 70° C. was filled again [boundary region 2], and lastly, 80 µl of the PBST solution was filled [reaction region 3]. The filling was performed in a perpendicularly standing state, and attention was paid so that air is not caught during filling. After the gel is filled, it was left for 15 minutes and then, the last PBST solution was added so as to fabricate the capillary.

To the capillary which is the simple measurement tool of the present invention fabricated as above, the Goat anti-mouse IgG AP immobilized antibody beads solution prepared in the reference example 5 is applied in a full amount to the reaction region 3.

The beads applied in the capillary were collected by the magnet and the beads were transferred from the PBST solution [reaction region 3] to the PNPP coloring reagent solution phase [reaction region 2] through the boundary region 2 composed of the above-described gelled substance, the magnet was removed once, the capillary was attached to the rotator and rotated for 15 minutes so that the beads were diffused in the solution and then, the beads were collected by the magnet again and transferred to the next solution-phase PBST solution [reaction region 1] through the boundary region 1 composed of the above-described gelled substance and lastly, it was confirmed that the PNPP coloring reagent solutions in the reaction region 2 was developed from transparent to yellow and it could be confirmed that AP conjugate Goat anti-mouse IgG were present in the beads and they reacted (FIG. 4).

In the prior-art coloring reagent, the reaction stopping reagent such as sodium hydroxide needs to be newly added in order to stop coloring in certain time, but the reaction is stopped in this reaction system by moving the beads and thus, a reaction result can be checked simply by moving the beads. Since the check was made visually, a degree of coloring cannot be confirmed easily in numerical values but it was confirmed that determination based on presence/absence (dark/pale) indicating whether it is at a detection limit or less or more can be made.

INDUSTRIAL APPLICABILITY

The simple measurement tool of the present invention can be of small-sized/light-weighted and/or disposable and various types of measurement, diagnosis or the like can be performed safely and easily in an environment without a special measurement device or the like such as outdoor or a site in a developing country or the like, for example, and therefore, it is expected to largely contribute to improvement of public health, solution of environmental problems and the like.

The invention claimed is:
1. An enzyme-linked immunosorbent assay (ELISA) simple measurement tool for a test substance, the tool comprising:
   a first region located on a first end of the simple measurement tool, said first region comprising a) magnetic particles carrying a primary antibody immobilized on a surface thereof against the test substance, and b) a first water-based liquid;

a second region comprising a) an enzyme-labelled secondary antibody, and b) a second water-based liquid;

a third region comprising a) a chromogenic substance, and b) a third water-based liquid;

a fourth region on a second end of the tool for receiving the magnetic particles from the third region, wherein the fourth region comprises a fourth water-based liquid and does not contain the chromogenic substance;

boundary regions comprising a gelling agent and a gel-type substance that is not or hardly soluble in the water-based liquid(s) and thus does not have a chemical influence on the water-based liquid(s), wherein the gel-type substance that is not or hardly soluble is an oily substance whose solubility to water at 25° C. is 100 ppm or less and in a liquid state at a normal temperature of 20° C.±15° C.; and a container holding the first, second, third and fourth regions and the boundary regions;

wherein the second region is located between the first and third regions and the third region is located between the second and fourth regions, wherein the first, second, third and fourth regions are each independent of each other, wherein each of the first, second, third and fourth regions are separated from each other via at least one boundary region;

wherein the magnetic particles can be substantially exclusively transferred using a magnet from the first region to the fourth region through at least three boundary regions separating those regions, while independence of the respective regions and the respective boundary regions as well as a function of the magnetic particles are maintained; and wherein the reaction of the chromogenic substance with an enzyme of the enzyme-labelled secondary antibody can be stopped by moving the magnetic particles from the third region to the fourth region.

2. The simple measurement tool according to claim 1, comprising further boundary region(s), each of which is independent.

3. The simple measurement tool according to claim 1 or 2, wherein a capacity of each first, second, third and fourth region is in a range of 10 to 100 µl.

4. The simple measurement tool according to claim 1, wherein, in the direction the magnetic particles are moved, a length of the boundary regions is 2 to 20 mm and a length of the regions is 10 to 80 mm.

5. The simple measurement tool according to claim 1, wherein the container is a cylindrical capillary having a diameter of 1.5 to 2.4 mm and a length of 75 to 125 mm.

6. The simple measurement tool according to claim 1, wherein the water-based liquids of at least two regions comprise compositions that are different from each other.

7. The simple measurement tool according to claim 1, wherein the magnetic particles are contained in an amount as low as 10 µg and up to 200 µg per the container.

8. The simple measurement tool according to claim 1, wherein the boundary regions have a storage viscoelastic modulus E' of 10 to 100 kPa at a normal temperature of 20° C.±15° C.

9. The simple measurement tool according to claim 1, wherein the boundary regions have a storage viscoelastic modulus E' of 20 to 50 kPa at a normal temperature of 20° C.±15° C.

10. The simple measurement tool according to claim 1, wherein the gel-type substance that is not or hardly soluble in the water-based liquid(s) comprises ester oil, hydrocarbon oil, or silicone oil.

11. The simple measurement tool according to claim 1, wherein the gel-type substance that is not or hardly soluble in the water-based liquid(s) comprises dimethypolysiloxane, methylphenylpolysiloxane, or methylhydrogenpolysiloxane.

12. A kit for manufacturing the tool of claim 1, said kit comprising:

magnetic particles carrying a primary antibody immobilized on a surface thereof;

an enzyme-labelled secondary antibody;

a chromogenic substance;

a water-based liquid;

a container capable of holding the first, second, third, and fourth regions, each comprising the water-based liquid, the regions being independent of each other;

a material capable of being a gel-type substance;

a gelling agent; and a sealing component capable of closing an end of the container, wherein the material capable of being a gel-type substance and gelling agent can form boundary regions, said boundary regions separating the first, second, third, and fourth regions, said boundary regions composed of a gel-type substance that is not or hardly soluble in the water-based liquid and thus does not have a chemical influence on the water-based liquid in adjacent regions, wherein the gel-type substance that is not or hardly soluble is an oily substance whose solubility to water at 25° C. is 100 ppm or less and in a liquid state at a normal temperature of 20° C.±15° C.; and wherein the magnetic particles can be substantially exclusively transferred using a magnet from the first region to the fourth region through at least three boundary regions separating these regions, while independence of the respective regions and the respective boundary regions as well as a function of the magnetic particles are maintained; and wherein the reaction of the chromogenic substance with an enzyme of the enzyme-labelled secondary antibody can be stopped by moving the magnetic particles from the third region to the fourth region.

13. The kit according to claim 9, wherein the gel-type substance comprises a silicone oil and the gelling agent comprises hydroxyl fatty acid, dextrin-fatty acid ester, or glycerin-fatty acid ester.

14. The kit according to claim 12, wherein the gel-type substance comprises a silicone oil and the gelling agent comprises glycerin-fatty acid ester.

15. An ELISA method for measuring a test substance using the simple measurement tool according to claim 1, comprising:

(a) contacting a sample with the primary antibody in the first region, wherein the test substance, if present in the sample, binds to the primary antibody;

(b) transferring the magnetic particles from the first region to the second region through at least one boundary region using a magnet, wherein a binding reaction with the enzyme-labelled secondary antibody can occur in the second region;

(c) transferring the magnetic particles from the second region to the third region through at least one boundary region using a magnet, wherein a chemical reaction with the chromogenic substance can occur in the third region;

(d) transferring the magnetic particles from the third region to the fourth region through at least one boundary region using the magnet, thereby stopping the chemical reaction; and (e) after the chemical reaction with the chromogenic substance is completed, measuring a result of the chemical reaction as indicative of the presence of the test substance.

\* \* \* \* \*